US005661138A

United States Patent [19]
Peterson et al.

[11] Patent Number: 5,661,138
[45] Date of Patent: Aug. 26, 1997

[54] (O-ACYL-P-N-ACYLAMINO-PHENYL)-O-PHOSPHOETHANOLAMINES

[75] Inventors: Andrew C. Peterson, Madison, Wis.; Rudolf Franzmair, Linz, Austria; Haridasan K. Nair, Madison, Wis.

[73] Assignee: Clarion Pharmaceutical, Inc., Madison, Wis.

[21] Appl. No.: 726,059

[22] Filed: Oct. 3, 1996

[51] Int. Cl.$^6$ .............................. A61K 31/685; C07F 9/10
[52] U.S. Cl. ........................ 514/77; 554/41; 558/166
[58] Field of Search .............................. 514/77; 558/166; 554/41

[56] References Cited

PUBLICATIONS

Bartlett, R.R., et al (1993), "Effects of leflunomide on immune responses and models of inflammation," Springer, Semin, *Immunopathol* 14:381–394.

Basil, B.; Clark, J. R.; Coffee, E.C.J.; Jordan, R.; Loveless, A.H.; Pain, D.L.; and Wooldridge, K.R.H., "A New Series of Cardioselective Adrenergic β-Receptor Blocking Compounds. 1–(2–Acyl–4–acylaminophenoxy(–3–isoprpylaminopropan–2–ols," *J. Med. Chem.* (1976) 19(3):399–402.

S.L. Kunkel, "Inflammatory Cytokines", pp. 1–15, in *Manual of Vascular Mediators.*, P.A. Ward, Editor, produced by the publishers of Hospital Practice (1994).

Luck, Michael S. and Bass, Paul, (1993), "Effect of Epidermal Growth Factor on Experimental Colitis in the Rat," *J. Pharmacol. Exp. Therap.* 264:984–990.

"Pharmacological Methods in the Control of Inflammation," Joseph Y. Chang and Alan J. Lewis (eds), Alan R. Liss, Inc., New York, pp. 221–223 (1989).

Ralph, Peter and Naloinz, I., "Antibody–Dependent Killing of Erythrocyte and Tumor Targets by Macrophage–Related Cell Lines: Enhancement by PPD and LPS," *J. Immunology* (1977) 119:950–954.

Raschke, W.C.; Baird, S.; Ralph, P., and Nakoinz, I., "Functional Macrophage Cell Lines Transformed by Abelson Leukemia Virus," *Cell* (1978) 15:261–267.

Raval, A.A. and Shah, N.M., "Studies in Chalcones and Related Compounds Derived from 2–Hydroxy–5–acetamino–acetophenone. III. Synthesis of 6–Amino–2–methylchromone and 6–Aminoflavone by the Claisen Reaction," *J. Org. Chem.* (1958) 23:748–749.

Raval, A.A. and Thakor, V.M., "Synthesis of a 2'–hydroxy–5'–propionamino–4–nitro–α–methyl Chalkone," *J. Indian. Chem. Soc.* (1961) 38(7):421–422.

Trush, M.A. et al, (1978), The generation of chemiluminscience by phagocytic cells, *Methods in Enzymology*, 56:462–494.

*Primary Examiner*—Joseph McKrane
*Attorney, Agent, or Firm*—DeWitt Ross & Stevens

[57] ABSTRACT

Novel (o-acyl-p-N-acylamino-phenyl)-O-phosphoethanolamines and pharmaceutically acceptable salts thereof having anti-inflammatory activity, and pharmaceutical compositions containing same are disclosed. Certain novel intermediates are also disclosed.

14 Claims, 3 Drawing Sheets

(O-ACYL-P-N-ACYLAMINO-PHENYL)-O-PHOSPHOETHANOLAMINES

The present invention relates to novel (o-acyl-p-N-acylamino-phenyl)-O-phosphoethanolamines, to pharmaceutically acceptable salts thereof, and to pharmaceutical compositions containing same. These novel compounds possess anti-inflammatory activity. The invention also encompasses certain novel intermediates.

DESCRIPTION OF THE INVENTION

Figure 1:
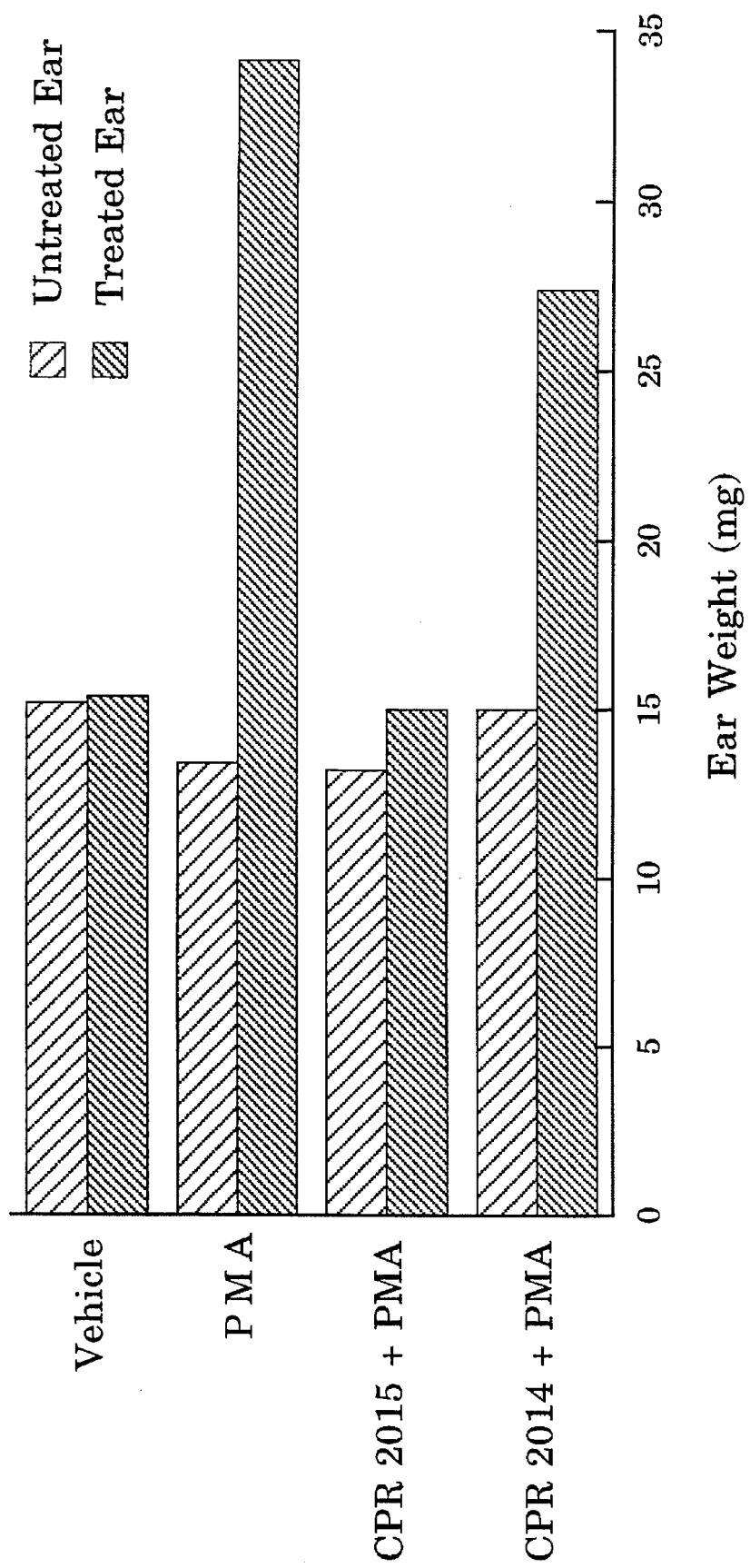
FIG. 1 is a graphical representation of results from an in vivo assay evaluating inhibition of PMA-induced inflammation in mouse ears by two compounds of the invention, designated CPR-2014 and CPR-2015.

The (o-acyl-p-N-acylamino-phenyl)-O-phosphoethanolamines of the subject invention are represented by Formula (I):

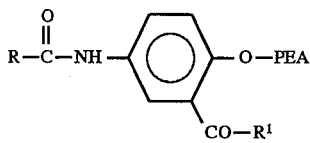

wherein:

R represents an unsubstituted or substituted linear or branched $C_{9-23}$ alkyl (preferred) or alkenyl, said substituent being one or more of halo, $C_{1-3}$ alkoxy or cyano, provided that a double bond of said alkenyl does not involve the carbon atom of said alkenyl that is bonded to the carbonyl (C=O) function of Formula I;

$R^1$ represents a linear or branched $C_{1-23}$ alkyl, optionally substituted as denoted for R; and O-PEA represents an O-phosphoethanolamine moiety of the formula:

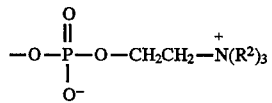

in which $R^2$ is hydrogen or methyl, provided that at least one $R^2$ is methyl.

When all three of said $R^2$ are methyl, the O-PEA moiety is denoted as a phosphocholine moiety; with two methyls, a phospho-(N,N-dimethyl)ethanolamine moiety; and with only one methyl, a phospho-(N-methyl)ethanolamine moiety.

As used herein, R is a linear (preferred) or branched $C_{9-23}$ alkyl such as, for example, nonyl, tetradecyl, pentadecyl, hexadecyl, heptadecyl, eicosyl and the like, including the branched analogs thereof. R is also a corresponding $C_{9-23}$ mono- (preferred) or polyunsaturated alkenyl, whereby a double bond of said alkenyl does not originate at the carbon atom bound to the carbonyl (C=O) function of Formula I. The preferred alkyl contains 13–19 carbons, particularly 15–17 carbons. Both the aforementioned alkyl and alkenyl may be substituted one or more times, preferably once, with substituents which do not interfere during the synthetic steps of making the subject compounds, preferably halo, hydroxy, $c_{1-33}$ alkoxy or cyano. As noted, $R^1$ is a linear (preferred) or branched $C_{1-23}$ alkyl ($C_{1-3}$ alkyl preferred), optionally substituted as denoted for R. The term "halo" refers to the halogens chloro, bromo, fluoro and iodo, with chloro and fluoro preferred.

The most preferred compounds of Formula (I) are those wherein R is $C_{15-17}$ alkyl, $R^1$ is methyl and O-PEA is the O-phosphocholine moiety, for example: (o-acetyl-p-N-octadecanamido-phenyl)-O-phosphocholine; and (o-acetyl-p-N-hexadecanamido-phenyl)-O-phosphocholine, the latter hereinafter also referred to as CPR-2015.

Other particular compounds of Formula (I) include:
(o-acetyl-p-N-tetradecanamido-phenyl)-O-phosphocholine;
(o-eicosanoyl-p-N-hexadecanamido-phenyl)-O-phosphocholine;
(o-tetracosanoyl-p-N-octadecanamido-phenyl)-O-phospho-(N-methyl)-ethanolamine;
{o-propionyl-p-(9-chloro-N-octadecanamido)-phenyl}-O-phospho-(N-methyl)-ethanolamine;
{o-decanoyl-p-(8-methoxy-N-hexadecanamido)-phenyl}-O-phospho-(N,N-dimethyl)-ethanolamine;
{o-acetyl-p-(9-cyano-N-octadecanamido)-phenyl}-O-phosphocholine;
(o-butyryl-p-N-octadecanamido-phenyl)-O-phospho-(N,N-dimethyl)-ethanolamine;
{o-acetyl-p-(8-trans-N-hexadecenamido)-phenyl}-O-phosphocholine;
(o-hexadecanoyl-p-N-hexadecanamido-phenyl)-O-phosphocholine;
{o-(9-chloro-octadecanoyl)-p-N-octadecanamido-phenyl}-O-phosphocholine;
{o-(8-methoxy-hexadecanoyl)-p-N-hexadecanamido-phenyl}-O-phosphocholine; and
{o-(9-cyano-octadecanoyl)-p-N-octadecanamido-phenyl}-O-phosphocholine.

CHEMISTRY

The compounds of Formula (I) may be prepared by the stepwise procedure outlined in the following reaction scheme (Et=$C_2H_5$) and the subsequent examples.

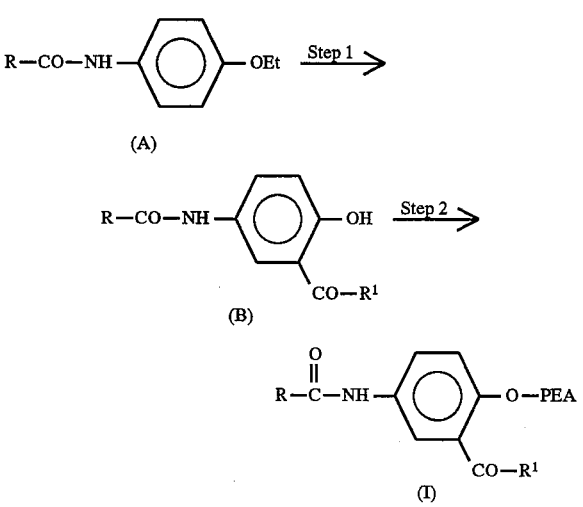

The thus-obtained compounds may be purified by conventional methods of the art, e.g., chromatography, recrystallization, etc.

Step 1:

The compounds of Formula (A) are generally known in the literature and are obtainable by art-recognized procedures. An exemplary procedure is the N-acylation of the known compound, p-phenetidine, using as the acylating agent an acyl chloride of the formula RCOCl, wherein R is as previously defined or the corresponding acid anhydride. Such N-acylation methodology is illustrated in Example (1) for the preparation of the known Formula (A) compound, p-(N-palmitoyl)-phenetidine.

The compounds of Formula (B) are readily obtained by the acylation of the Formula (A) compounds with an appropriate acylating agent, such as an acyl chloride of the formula $R^1COCl$, wherein $R^1$ is as previously defined or the corresponding acid anhydride. For example, the acyl chloride, dissolved in a cooled (10°–20° C.) inert aprotic solvent such as nitromethane, preferably containing aluminum chloride, is slowly added to a cooled solution of the Formula (A) compound in the same solvent to yield the Formula (B) compound.

Step 2:

The phosphoethanolamine moiety (PEA) is introduced by the reaction of the hydroxyl group in compound (B) with 2-chloro-2-oxo-1,3,2-dioxaphospholane in an inert organic aprotic solvent, such as, for example, toluene (preferred), benzene, chloroform, diethyl ether, dioxane and the like, followed by reaction with an appropriate amine, $N(R^2)_3$ to yield the desired compound (I).

It is recognized that cis and trans geometric isomers may also be present in the subject compounds, e.g., when R in Formula (I) is alkenyl, due to the cis and trans configuration inherent with the double bond. Thus, by initially starting with an appropriate cis or trans precursor, the corresponding end product of the Formula (I) compound will be obtained. All such isomers are intended to be within the scope of this invention.

Several o-acyl-p-N-acylamino-phenols, similar to Formula (B), have been reported in the literature, wherein R and $R^1$ are lower alkyl. For example, J. Org. Chem. (1958) 23:748–749, discloses $R=R^1=Me$; J. Indian Chem. Soc. (1961) 38(7):421–422, discloses $R=R^1=Et$; and J. Med. Chem. (1976) 19(3):399–402, discloses $R=C_{1-7}$ alkyl and $R^1=C_{1-3}$ alkyl.

Figure 3:
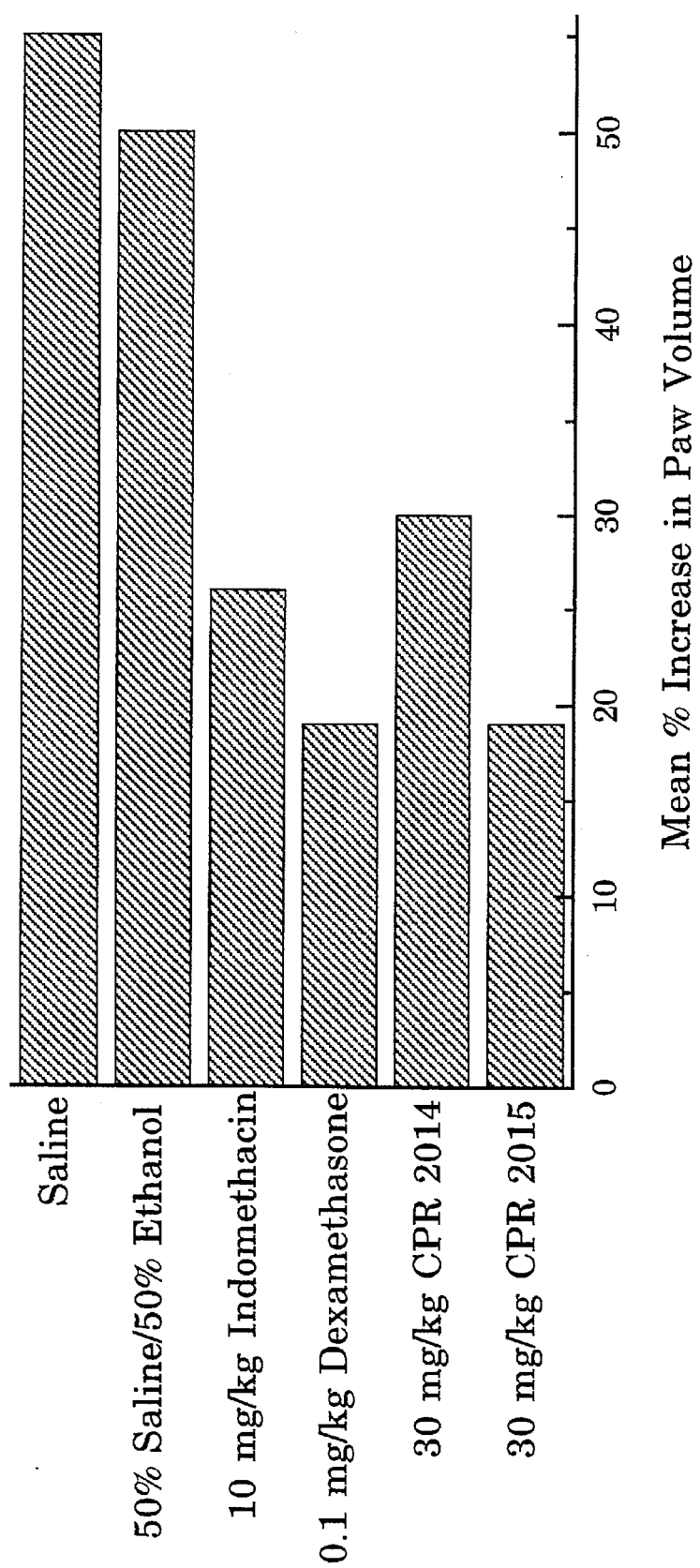
FIG. 3 is a graphical representation of results from an in vivo assay evaluating the inhibitory effect of CPR-2014 and CPR-2015 on carrageenan-induced paw edema in the rat.

It is believed, however, that the literature has not heretofore reported those Formula (B) type compounds wherein R is the fatty $C_{9-3}$ groups previously described, more particularly the $C_{13-19}$ fatty groups and most particularly the $C_{15-17}$ fatty groups, and $R^1$ is as previously described. Accordingly, such novel compounds constitute an additional aspect of the present invention. In addition to their utility as reaction intermediates, anti-inflammatory activity has also been found, although of lessor potency than the Formula (I) compounds. See, for example, the results illustrated in FIG. 1 and in FIG. 3 for the Formula (B) compound 1-(5-hexadecanamido-2-hydroxy-phenyl)-ethanone, also referred to as CPR-2014.

The invention also comprehends salts of the Formula (I) compounds. These salts include acid addition salts such as, for example, those made from inorganic acids such as hydrochloric, nitric, and the like acids or from organic acids such as citric, lactic and the like acids. The salts also include those made with bases such as, for example, sodium and potassium hydroxide. The salts of the invention are made by conventional methods well known to those skilled in the art. The salts for therapeutic use of the Formula (I) compounds are pharmaceutically acceptable salts, as well understood in the art.

ANTI-INFLAMMATORY UTILITY

The anti-inflammatory activity of the herein-described compounds of Formula (1) and pharmaceutically acceptable salts thereof may be assayed by many ways conventional in the art. Four such assays are described here.

A. In Vitro Chemiluminescence Assay.

Inflammation is a complex process, involving a variety of cell types including macrophages, for example, see S. L. Kunkel, "Inflammatory Cytokines", pp. 1–15, in Manual of Vascular Mediators,. P. A. Ward, Editor, produced by the publishers of Hospital Practice. References relative to macrophages are numerous, including, for example, J. Immunology (1977) 119:950–954, and Cell (1978) 15:261–267.

Macrophages are activated by injection and by a wide variety of noninfectious irritants and proinflammatory agents. Upon activation, macrophages participate in a variety of reactions. They may phagocytose bacteria and kill them by either oxygen dependent or independent pathways. They are activated to increase oxygen consumption and production of reactive oxygen species (for example, superoxide). In addition, they release a variety of inflammatory cytokines, including several interleukins and tumor necrosis factor $\alpha$ (TNF$\alpha$). Inhibition of any of these pathways can lead to reduced inflammation.

The RAW 264.7 cell line (ATCC TIB 71) is a murine monocyte/macrophage line that shows many of the differentiative functions of a macrophage. The cells are capable of phagocytosis and undergo an oxidative burst in response to appropriate signals. Agents that inhibit the activation of these cell in vitro are therefore inhibitors of critical steps in inflammatory processes.

Activation of macrophages and other phagocytic cell types initiates a cascade of actions that include increased oxygen consumption (respiratory burst) and production of oxygen radicals. These events can be measured m a variety of ways, including chemiluminescence based on the addition of luminol (see M. A. Trush et al, (1978), The generation of chemiluminescence by phagocytic cells, Methods in Enzymology 56:462–494). Because chemiluminescence is induced by the increased production of oxygen radicals that are thought to be important in intracellular killing of bacteria, chemiluminescence has long been used as an index of phagocytic cell activity. In addition, oxygen radical production is associated with inflammatory responses and may have adverse consequences in non-infectious inflammation. For this reason, macrophage activation is of critical importance in studies of the inflammatory process. Agents that reduce macrophage activation are likely to have utility as anti-inflammatory agents. Since luminescence generated from luminol is a recognized marker of macrophage activation, the finding that the subject compounds of Formula (I) strongly inhibit chemiluminescence in macrophages correlates to their usefulness in ameliorating intimation.

1. Cell line: Raw 264.7 (ATCC TIB-71, attachment dependent).
2. Culture medium: Dulbecco's Modified Eagle's Medium (DMEM) with 10% Fetal Bovine Serum (FBS).
3. Standard protocol for culturing cell lines: in T-75 or T-150 flasks; 37° C.; 95% air, 5% $CO_2$; 100% humidity;
    a. Cell line is passaged when approximately 80% confluent; with trypsin (1 mg/mL) and ethylenediaminetetraacetic acid (EDTA) (1 mM in Ca-Mg free Hank's balanced salt solution); at a 1:4 to 1:5 split;

b. All procedures are performed aseptically in a class II biological safety cabinet using standard BL-2 containment procedures. In order to prevent genetic drift in stock cell lines, fresh cultures are prepared at approximately monthly intervals with cells thawed from liquid nitrogen storage.

4. Methodology:
   a. After cell passage, count cells with a hemacytometer;
   b. Adjust cell concentration to approximately 1,000,000 cells per mL;
   c. Suspend cells in DMEM lacking phenol red and without FBS;
   d. Pipette 1 mL of cell suspension into a standard luminometer cuvette (12×75 mm), commercially obtainable from Analytical Luminescence Laboratories, San Diego, Calif., USA;
   e. Add luminol to final concentration of 0.2 mM;
   f. Add test compound dissolved in phosphate buffered saline (PBS) for final concentration levels ranging from 0 to 10 µM;
   g. Add 100 nanograms of phorbol myristate acetate (PMA): and
   h. Wait 1 minute and read photo counts (i.e., luminescence) on a Monolight 2010 luminometer available from Analytical Luminescence Laboratories, San Diego.

5. Data Analysis:
   Background—no test compound present; no PMA present;
   Control—no test compound present;
   Calculate:

$$\% \text{ Inhibition} = \frac{(1 - L(\text{test compound}) - L(\text{background}))}{L(\text{control}) - L(\text{background})} \times 100$$

where L is luminescence.

6. Results are represented in Table 1, which indicates the marked inhibition of PMA-induced macrophage activation by CPR-2015 at concentrations above 0.3 µM.

TABLE 1

Inhibition of Resipiratory Burst in PMA-Stimulated Mouse Macrophage RAW 264.7

| Concentration (mM) | % Inhibition CPR-2015 |
|---|---|
| 10 | 99 |
| 3 | 97 |
| 1 | 94 |
| 0.3 | 63 |
| 0.1 | 13 |

B. In Vivo Assay—Mouse Ear Intimation Model

A common in vivo model for the evaluation of anti-inflammatory agents is PMA-induced inflammation in mouse ears. This method is described in "Pharmacological Methods in the Control of Inflammation," Joseph Y. Chang and Alan J. Lewis (eds), Alan R. Liss, Inc., New York, pp 221–223 (1989). In this assay, edema, which is a characteristic of inflammation, is quantified by determining ear thickness or ear weight approximately 6 hours after applying PMA to the ear.

1. Mice: Male CD-1, 21–24 g (Product Number 3002) obtainable from Harlan Sprague Dawley, Indianapolis, Ind., USA.
2. Methodology:
   a. Prepare 0.01% (w/v) PMA in a mixture of equal volumes of acetone and ethanol;
   b. Prepare 0.01% (w/v) PMA and 5% (w/v) test compound in a mixture of equal volumes of acetone and ethanol;
   c. Divide 12 mice into 4 groups of 3 mice each;
   d. Treat the first group of mice by applying 20 µL of a mixture of equal volumes of acetone and ethanol (vehicle) to the left ear using a micropipetter;
   e. Treat the second group of mice by applying 20 µL of PMA solution to the left ear;
   f. Treat the other two groups of mice by applying 20 µL of PMA/test compound solution to the left ear;
   g. Wait 6 hours and euthanize the mice in a $CO_2$ chamber;
   h. Cut the ears and punch out circles of 6-mm diameter; and
   i. Measure the weight of three appropriate ear punches in the same group together.

3. Results are illustrated in FIG. 1. At the concentration tested (5%), CPR-2015 completely inhibited and CPR-2014 partially inhibited PMA-induced intimation in mouse ear.

C. In Vivo Assay—Rat Ulcerative Colitis Model

The model described in this section provides a tool for investigating the effect of compounds in colonic intimation. This model and the experimental methods are described in the following reference: Luck, Michael S. and Bass, Paul, (1993), "Effect of Epidermal Growth Factor on Experimental Colitis in the Rat," *J. Pharmacol. Exp. Therap.* 264:984–990. In this assay, inflammatory lesions in the rat colon are induced by the intracolonic administration of 2,4,6-trinitrobenzenesulfonic acid.

1. Rats: Male Sprague-Dawley, 185–195 g obtainable from Harlan Sprague Dawley, Indianapolis, Ind., USA;
2. Methodology:
   a. Prepare 100 mg/mL 5-aminosalicylic acid (5-ASA), 50 mg/mL CPR-2015, and 150 mg/mL CPR-2015 in saline;
   b. Divide 34 rats into 4 groups of 8 rats each and one group of two rats;
   c. Leave the group with two rats completely untreated;
   d. Treat the other four groups of rats with 200 µl of Saline, 500 µl of 100 mg/mL 5-ASA, 200 µl of 50 mg/mL CPR-2015, or 200 µl of 150 mg/mL CPR-2015. These treatments are administered rectally with an 8-cm catheter;
   e. After one hour, treat the above four groups of rats rectally with 500 µl of 100 mg/mL 2,4,6-trinitrobenzenesulfonic acid (TNB) in 30% ethanol and 70% saline;
   f. Repeat the treatments described in paragraph 2(d) once a day for a total of 5 days;
   g. On the 6th day, euthanize the rates in a $CO_2$ chamber; and
   h. Remove the colons and rank on a 0–5 scale based on lesion and thickness, 0 being a normal colon, and 5 being the most severely damaged colon.

Figure 2:
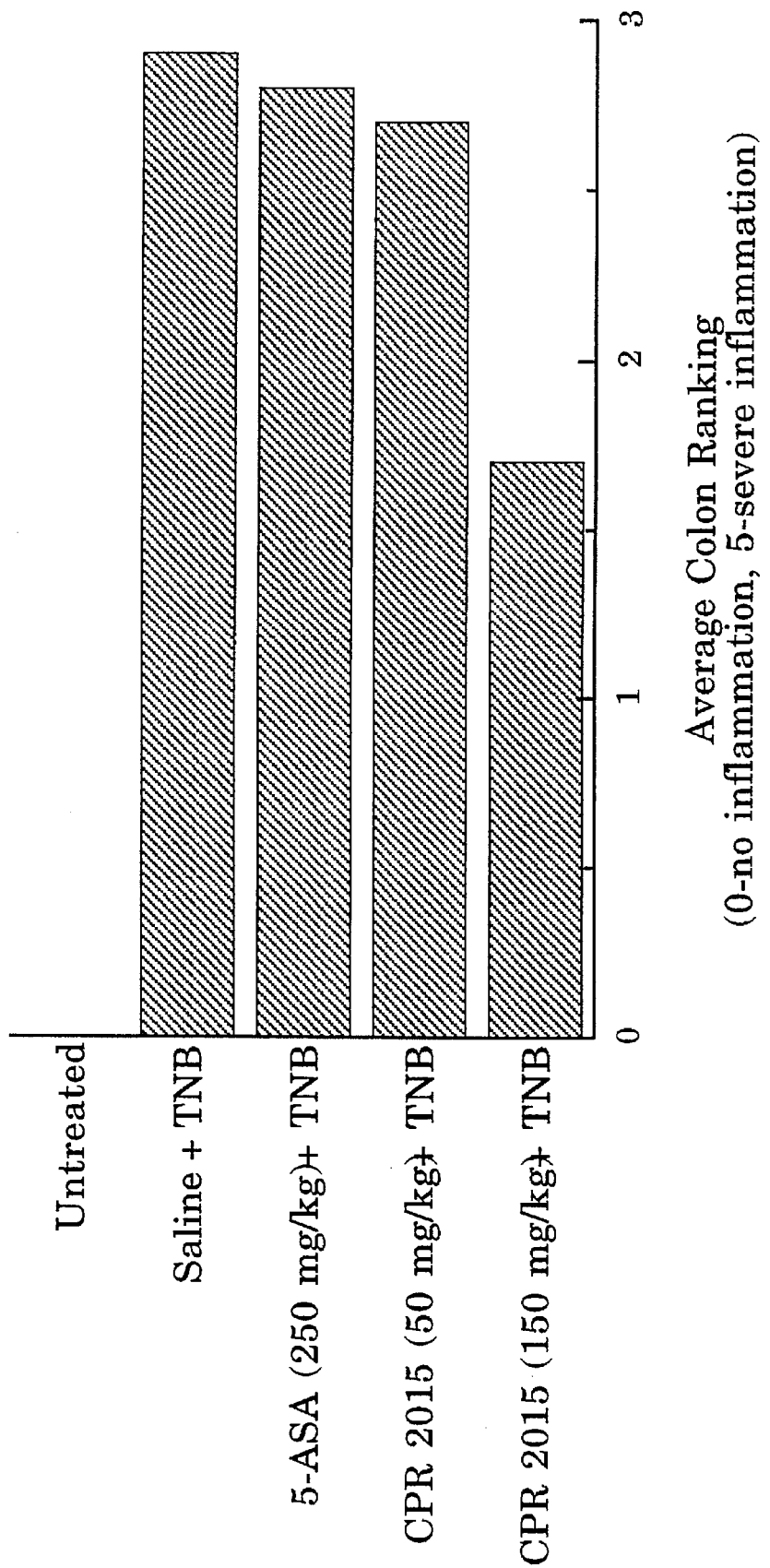
FIG. 2 is a graphical representation of results from an in vivo assay evaluating inhibition of TNB-induced inflammation in rat colon by CPR-2015.

3. Results are illustrated in FIG. 2, which shows the marked inhibition of TNB-induced intimation in rat colon by CPR-2015 at 150 mg/kg.

D. In Vivo Assay—Rat Carrageenan-Induced Paw Edema.

The model, which provides a tool for investigating the effect of compounds on paw intimation, is described in the following reference: Bartlett, R. R., et al. (1993), "Effects of leflunomide on immune responses and models of inflammation," Springer Semin Immunopathol 14:381–394. It essentially consists of the following:

1. Rats: Male Sprague-Dawley, approximately 165 g obtainable from Harlan Sprague Dawley, Indianapolis, Ind., USA;

2. Methodology:
   a. Measure the volume of the left hind paw by strain gauge/fluid immersion;
   b. Inject 100 μL of 1% carrageenan in saline intradermally into the left hind foot pad;
   c. Inject vehicles or test compounds dissolved in either saline (CPR-2015) or 50% saline and 50% ethanol (indomethacin, dexamethasone, and CPR-2014) intraperitoneally, placing 3–5 rats in each treatment group;
   d. Six hours later, measure the volume of the left hind paw by strain gauge/fluid immersion;
   e. Calculate average percent increase in paw volume for each treatment group.
3. Results are presented in FIG. 3, which demonstrates the marked inhibition of carrageenan-induced edema in rat paw by CPR-2014 and CPR-2015.

The positive results obtained in the foregoing in vitro and in vivo assays are illustrative of the anti-inflammatory activity the Formula (I) compounds.

The instant invention thus provides a method of treating inflammation in a mammal afflicted with same comprising administering to said mammal an effective anti-inflammatory amount of a compound of Formula (I) or a pharmaceutically acceptable salt thereof. It also provides pharmaceutical compositions comprising an effective anti-inflammatory amount of a compound of formula (I) or a pharmaceutically acceptable salt thereof and a pharmaceutically acceptable carrier.

PHARMACEUTICAL COMPOSITIONS

Pharmaceutical compositions of the present invention, for medical use, comprise an active compound, i.e., a Formula (I) compound or a pharmaceutically acceptable salt thereof, together with an acceptable carrier therefor and optionally other therapeutically active ingredients. The carrier must be pharmaceutically acceptable in the sense of being compatible with the other ingredients of the formulation and not deleterious to the recipient thereof.

The formulations include those suitable for oral, topical, rectal or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier and one or more optional accessory ingredients. In general, the formulations are prepared by uniformly and intimately bringing the active compound into association with a liquid or solid carrier and then, if necessary, shaping the product into desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as suspension, solution, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

Formulation suitable for parenteral administration conveniently comprise a sterile preparation of the active compound in, for example, a polyethylene glycol 200 or propylene glycol solution which is preferably isotonic with the blood of the recipient.

Useful formulation also comprise concentrated solutions or solids containing the compound of Formula (1) which upon dilution with an appropriate solvent give a solution suitable for parenteral administration.

Preparations for topical or local applications comprise aerosol sprays, lotions, gels, ointments, etc., and pharmaceutically acceptable vehicles therefore such as, for example, lower aliphatic alcohols, polyglycerols such as glycerol, polyethylene glycerol, esters of fatty acids, oils and fats, silicones, and other conventional topical carders. In topical formulations, the compounds of Formula (1) are preferable utilized at concentrations of from about 0.1% to about 5.0% by weight.

In addition to the aforementioned ingredients, the formulations of this invention may further include one or more optional accessory ingredient(s) utilized in the art of pharmaceutical formulations, e.g., diluents, buffers, flavoring agents, colorants, binders, surface active agents, thickeners, lubricants, suspending agents, preservatives (including antioxidants) and the like.

The amount of compound of Formula (1) required to be effective for each of the indicated activities will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective dose is in the range of about 0.1 to about 200 mg/kg body weight per day, preferably in the range of about 1 to about 100 mg/kg per day, calculated as the non-salt form of Formula (I). The total daily dose may be given as a single dose, multiple doses, e.g., two to six times per day, or by intravenous infusion for a selected duration. Dosages above or below the range cited above are within the scope of the present invention and may be administered to the individual patient if desired and necessary. In general, the pharmaceutical compositions of this invention contain from about 0.5 to about 500 mg and, preferably, from about 5 to about 350 mg of the active ingredient, preferably in a unit dosage form.

For example, for a 75 kg mammal, a dose range would be about 7.5 to about 1500 mg per day, and a typical dose would be about 800 mg per day. If discrete multiple doses are indicated, treatment might typically be 200 mg of a compound of Formula (I) given 4 times per day.

The following examples are intended to illustrate and not to limit the scope of the present invention. Unless otherwise specified, the indicated R and $R^1$ groups are linear.

EXAMPLE 1

P-(N-Palmitoyl)-phenetidine, also denoted as 4-(N-Hexadecanoyl)-phenetidine:

To 41.15 grams (0.3 mol) fleshly distilled p-phenetidine in 600 mL acetone is added, with stirring, 41.64 grams (0.3 mol) potassium carbonate and 82.46 grams (0.3 mol) palmitoyl acid chloride within one hour. The temperature is maintained within 20°–29° C. by cooling in a water bath. Additional acetone, up to 200 mL, may be added if necessary to achieve dissolution. Stirring is continued for about three hours at room temperature (18°–25° C.) and about 800 mL water are then added with stirring for thirty minutes. The resultant crystalline precipitate is filtered off, washed with water, and suspended in 1 liter water and then acidified with 0.1N hydrochloric acid until pH 4. The crystals are filtered off, washed with water until neutral, find air-dried to yield the titled product, p-(N-palmitoyl)phenetidine.

Purification is achieved by recrystallization from ethanol, filtration over a glass filter, washing with hot ethanol and cooling the filtrate to room temperature. The resultant precipitate is filtered off, washed with ethanol and petroleum ether, and dried to yield about 99.9 grams (88.7% theory) of product. To free the product of any residual ethanol (and any water), about 99.7 grams of product are dissolved in 600 mL toluene. Approximately 100 mL toluene are distilled off and the remaining solution is cooled to room temperature. The resultant precipitate of p-(N-palmitoyl)-phenetidine is filtered off and air-dried to yield about 97.4 grams (86.4% theory) of pure product.

EXAMPLE 2

The procedure of Example 1 is followed except that an equivalent amount each of decanoyl chloride, tetradecanoyl chloride, octadecanoyl chloride, 9-cis-octadecenoyl chloride and eicosanoyl chloride is used as the N-acylating agent in lieu of the palmitoyl chloride to yield, as respective products, the corresponding p-(N-acyl)-phenetidines of Formula (A).

EXAMPLE 3

1-(5-Hexadecanamido-2-hydroxy-phenyl)-ethanone, also denoted as o-Acetyl-p-hexadecanamido-phenol, or 1-(5-N-Hexadecylamino-2-hydroxy-phenyl)-ethanone:

Acetyl chloride (18.81 g, 0.2396 mol) is added slowly to a cooled (ice-water bath, 15°–18° C.) solution of aluminum chloride (63.9 g, 0.4792 mol) in nitromethane (300 mL) over a 10 minute period. 4-(N-Hexadecanoyl)-phenetidine (60 g, 0.1597 mol) is added in portions to the cooled nitromethane solution (ice-water bath, 15°–18° C.) over a 45 minute period. The resultant reaction mixture is warmed and stirred at 28°–30° C. for 1.5 h. The reaction mixture is poured into slowly stirred ice-water (600 mL); the product crystallizes. The crystallized product is filtered after 45 minutes, washed with water and petroleum ether, and then dried. The crystallized product (61.3 g) is recrystallized from 2-propanol (300 mL) overnight, filtered, washed with 2-propanol and petroleum ether, and dried. The resultant recrystallized product (56.8 g) is mixed with chloroform (250 mL), and the resultant slurry is heated at reflux. After cooling the slurry to room temperature over a 5 hour period, the slurry is filtered, washed with chloroform and diethyl ether, chromatographed and dried to yield the purified 1-(5-hexadecanamido-2-hydroxy-phenyl)ethanone (40.7 g, 39.5%): TLC (silica gel 60) 5:1 benzene:$CH_3OH$ ($R_f$=0.53); mp 120°–122° C.

EXAMPLE 4

By following the acylation procedure of Example 3, except that an equivalent amount of an appropriate acyl chloride is utilized as the acylating agent to acylate an equivalent amount of the appropriate Formula (A) compound, the following respective compounds of Formula (B) are obtained:

o-acetyl-p-octadecanamido-phenol;
o-butyryl-p-tetradecanamido-phenol;
o-decanoyl-p-decanamido-phenol;
o-tetradecanoyl-p-(9-cis-octadecenamido)-phenol;
o-octadecanoyl-p-eicosanamido-phenol; and
o-acetyl-p-tetraeicosanamido-phenol.

EXAMPLE 5

1-(5-Hexadecanamido-2-O-phosphocholine-phenyl)-ethanone, also denoted as (o-acetyl-p-hexadecanamido-phenyl)-O-phosphocholine, or (o-acetyl-p-N-hexadecylamino-phenyl)-O-phosphocholine:

Neat 2-chloro-2-oxo-1,3,2-dioxaphospholane (3.38 g, 24 mmol) is added in one portion to a stirred mixture of 1-(5-N-hexadecylamino-2-hydroxy-phenyl)-ethanone (10 g, 25.7 mmol) and triethylamine (7.9 mL, 56.8 mmol) in anhydrous toluene (400 mL) under a nitrogen atmosphere. The resultant mixture is stirred at room temperature for four days. The white solid which precipitates is filtered off and washed with dry toluene (100 mL). The toluene filtrate is concentrated in vacuo to leave a viscous residue which is further dried under high vacuum. Then, a mixture of trimethylamine (31 g) in acetonitrile (dried by distillation over phosphorus pentoxide, 325 mL) is added to the residue. The flask which contains the residue and trimethylamine in acetonitrile is sealed by tightly connecting the glass stopper to the flask with wire and is then heated with stirring to 60°–70° C. for 24 hours. Upon cooling, a white solid precipitates. The mixture is put into a refrigerator for 24 hours to further crystallization. The white solid precipitate is filtered from the cold solution and is washed sequentially with dry acetonitrile and acetone. The filtered solid is thoroughly dried under high vacuum. This white solid material is purified by column chromatography on silica gel to yield 1-(5-Hexadecanamido-2-O-phosphocholine-phenyl)ethanone, thoroughly dried under vacuum to provide 5.62 g (39.5%): TLC (silica gel 60) 70:30:5 $CHCl_3$:$CH_3OH$:30% aqueous ammonia ($R_f$=0.21); mp 179°–180° C.

EXAMPLE 6

The phosphoethanolaminization procedure of Example 5 is followed except that an equivalent amount of the appropriate Formula (B) compound of Example 4 and an equivalent amount of the appropriate amine, $N(R^2)_3$ are utilized to yield the following respective corresponding compounds of Formula (I):

(o-acetyl-p-octadecanamido-phenyl)-O-phosphocholine;
(o-butyryl-p-tetradecanamido-phenyl)-O-phospho-(N-methyl)-ethanolamine;
(o-decanoyl-p-decanamido-phenyl)-O-phosphocholine;
{o-tetradecanoyl-p-(9-cis-octadecenamido)-phenyl}-O-phosphocholine;
(o-octadecanoyl-p-N-eico sylamino-phenyl)-O-phospho-(N,N-dimethyl)-ethanolamine;
and
(o-acetyl-p-N-tetraeicosylamino-phenyl)-O-phospho-(N-methyl)-ethanolamine.

EXAMPLE 7

This is an illustrative example of tablets containing the following ingredients which may be prepared in a conventional manner:

| Ingredients | Per Tablet (mg) |
| --- | --- |
| CPR-2015 | 50–100 |
| Lactose | 70 |
| Maize starch | 70 |

11
-continued

| Ingredients | Per Tablet (mg) |
| --- | --- |
| Polyvinylpyrrolidone | 5 |
| Magnesium stearate | 5 |
| Tablet weight | 200–250 |

EXAMPLE 8

An illustrative oil-in-water cream base formulation for topical use:

| Ingredients | Grams |
| --- | --- |
| CPR-2015 | 10.0 |
| Anhydrous lanolin | 20.0 |
| Polysorbate 60 | 4.0 |
| Sorbitan monopalmitate | 2.0 |
| Light liquid paraffin | 4.0 |
| Propylene glycol | 5.0 |
| Methyl hydroxybenzoate | 0.1 |
| Purified water, to | 100.0 |

What is claimed:

1. An (o-acyl-p-N-acylamino-phenyl)-O-phosphoethanolamine of the formula:

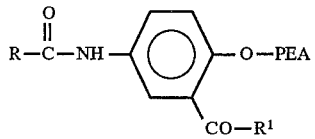

(I)

wherein:

R represents a linear or branched $C_{9-23}$ alkyl or alkenyl, optionally substituted with one or more of halo, $C_{1-3}$ alkoxy or cyano, provided that a double bond of said alkenyl does not involve the carbon atom of said alkenyl that is bonded to the C=O function of Formula I;

$R^1$ represents a linear or branched $C_{1-23}$ alkyl, optionally substituted as denoted for R; and O-PEA represents an O-phosphoethanolamine moiety of the formula:

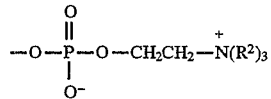

in which $R^2$ is hydrogen or methyl, provided that at least one $R^2$ is methyl; and the cis and trans isomers of (1) when R is said alkenyl; and the pharmaceutically acceptable salts thereof.

2. A compound of claim 1 wherein said R is $C_{13-19}$ alkyl and said $R^1$ is $C_{1-3}$ alkyl.

3. A compound of claim 1 wherein said R is $C_{15-17}$ alkyl and said $R^1$ is $C_{1-3}$ alkyl.

4. (o-acetyl-p-N-hexadecanamido-phenyl)-O-phosphocholine.

5. A method of treating intimation in a mammal afflicted with same which comprises administering to said mammal an effective anti-inflammatory amount of a phosphoethanolamine of claim 1.

6. The method of claim 5 wherein R and $R^1$ of said phosphoethanolamine are $C_{13-19}$ alkyl and $C_{1-3}$ alkyl, respectively.

7. The method of claim 5 wherein R and $R^1$ of said phosphoethanolamine are $C_{15-17}$ alkyl and $C_{1-3}$, alkyl, respectively.

8. The method of claim 5 wherein said phosphoethanolamine is (o-acetyl-p-N-hexadecanamido-phenyl)-O-phosphocholine.

9. A pharmaceutical composition comprising an effective anti-inflammatory amount of a phosphoethanolamine of claim 1 and a pharmaceutically acceptable carrier.

10. The pharmaceutical composition of claim 9 wherein R and $R^1$ of said phosphoethanolamine are $C_{13-19}$ alkyl and $C_{1-3}$, alkyl, respectively.

11. The pharmaceutical composition of claim 9 wherein R and $R^1$ of said phosphoethanolamine are $C_{15-17}$ alkyl and $C_{1-3}$ alkyl, respectively.

12. The pharmaceutical composition of claim 9 wherein said phosphoethanolamine is (o-acetyl-p-N-hexadecanamido-phenyl)-O-phosphocholine.

13. An o-acyl-p-N-acylamino-phenol of Formula (II):

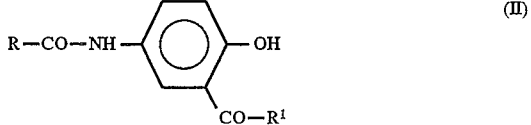

(II)

wherein R represents a linear or branched $C_{9-23}$ alkyl or alkenyl, optionally substituted with one or more of halo, $C_{1-3}$ alkoxy or cyano, provided that a double bond of said alkenyl does not involve the carbon atom of said alkenyl that is bonded to the C=O function of Formula II; $R^1$ represents a linear or branched $C_{1-23}$ alkyl, optionally substituted as denoted for R; and the cis and trans isomers of (II) when R is said alkenyl.

14. 1-(5-Hexadecanamido-2-hydroxy-phenyl)-ethanone.

* * * * *

UNITED STATES PATENT AND TRADEMARK OFFICE
CERTIFICATE OF CORRECTION

PATENT NO : 5,661,138
DATED : August 26, 1997
INVENTOR(S): Peterson, A.C.; Franzmair, R.; Nair, H.K.

It is certified that error appears in the above-identified patent and that said Letters Patent is hereby corrected as shown below:

On the cover page:
    in item 73 (Assignee), please delete "Clarion Pharmaceutical, Inc." and insert therefor --Clarion Pharmaceuticals Inc.--;
    in the designation of Primary Examiner, please delete "Joseph McKrane" and insert therefor --Joseph McKane--;
    in the designation of Attorney, Agent, or Firm, please delete "DeWitt Ross & Stevens" and insert therefor --DeWitt Ross & Stevens, S.C.--

At col. 3, line 46, please delete "$C_{9-3}$" and insert therefor --$C_{9-23}$--.

At col. 4, line 15, please delete "injection" and insert therefor --infection--.

At col. 5, line 52, please delete "Intimation" and insert therefor --Inflammation--.

At col. 6, lines 23, 56, and 60, please delete "intimation" and insert therefor --inflammation--.

At col. 9, line 5, please delete "find" and insert therefor --and--.

At col. 11, line 51 (*i.e.*, claim 1, line 17), please delete "(1)" and insert therefor --(I)--;
    at line 52 (*i.e.*, claim 1, line 18), please delete "said".

UNITED STATES PATENT AND TRADEMARK OFFICE
CERTIFICATE OF CORRECTION

PATENT NO : 5,661,138
DATED : August 26, 1997
INVENTOR(S): Peterson, A.C.; Franzmair, R.; Nair, H.K.

It is certified that error appears in the above-identified patent and that said Letters Patent is hereby corrected as shown below:

At col 12, lines 1-2 and 3-4, please delete "said";

at line 6 (i.e., claim 4, line 1), please delete "acetyl" and insert therefor --Acetyl--;
    at line 8 (*i.e.*, claim 5, line 1), please delete "intimation" and insert therefor --inflammation--.

Signed and Sealed this

Third Day of March, 1998

*Attest:*

BRUCE LEHMAN

*Attesting Officer*     *Commissioner of Patents and Trademarks*